United States Patent

Savage et al.

[11] Patent Number: 5,997,465
[45] Date of Patent: Dec. 7, 1999

[54] DEVICE FOR EXERTING AN EXTERNAL PRESSURE ON A HUMAN BODY

[75] Inventors: Steven J. Savage, Järfälla; Willy Johansson, Linköping, both of Sweden

[73] Assignee: FFV Aerotech AB, Linkoping, Sweden

[21] Appl. No.: 08/714,125

[22] PCT Filed: Mar. 17, 1995

[86] PCT No.: PCT/SE95/00277

§ 371 Date: Nov. 7, 1996

§ 102(e) Date: Nov. 7, 1996

[87] PCT Pub. No.: WO95/25038

PCT Pub. Date: Sep. 21, 1995

[30] Foreign Application Priority Data

Mar. 17, 1994 [SE] Sweden ................................ 9400897

[51] Int. Cl.$^6$ .............................. B64D 10/00; B64G 6/00
[52] U.S. Cl. .............................................................. 600/20
[58] Field of Search ........................ 600/19–20; 128/897

[56] References Cited

U.S. PATENT DOCUMENTS 3,820,162  6/1974  McGrew ................................ 2/2.1 A
5,153,938  10/1992  Epperson ................................ 2/2.1 A

FOREIGN PATENT DOCUMENTS

89/10871  11/1989  WIPO .

*Primary Examiner*—John P. Lacyk
*Attorney, Agent, or Firm*—Jacobson, Price, Holman & Stern, PLLC

[57] ABSTRACT

The invention relates to a device (1, 3, 37) for exerting an external pressure on a human body part. The device, which is designed to surround the body part with comfortable fit, comprises components (15, 19 and 28) of memory material, such as memory metal. By heating the components, e.g. by conducting electric current through them, they will assume a different shape, e.g. a shorter length, the device being adapted to be contracted so as to "squeeze" the body part. When the components are thereafter cooled, they will resume their previous shape and the contraction ceases. The device is intended, inter alia, to prevent pooling of blood in body parts of a pilot when subjected to G-forces, and to increase, by recurring contractions, the blood circulation in the body parts surrounded by the device.

31 Claims, 3 Drawing Sheets

DEVICE FOR EXERTING AN EXTERNAL PRESSURE ON A HUMAN BODY

BACKGROUND OF THE INVENTION

1. Field of the Invention

The present invention relates to a device for exerting an external pressure on parts of a human body, more specifically, the present invention relates to a device designed to surround a body part so as, for example to make it easier for pilots to withstand the high acceleration forces to which they are subjected when making abrupt turns with high-performance aircraft or to improve the blood circulation in people having poor cardiac activity. In the first instance, the device is of the type which prevents blood from being drained from the brain, primarily to the arms, legs and the lower part of the torso, by exerting a pressure on these parts so as to prevent them from swelling and receiving additional blood. In the second instance, the device is of the type which "squeezes" the patient's legs at a certain rhythm to increase the blood flow therein.

2. Background of the Prior Art

Pilots who perform rapid changes of direction when flying at high speeds, are subjected to considerable acceleration forces, so-called G-forces. These cause blood to be driven away from the brain and out into the limbs and the lower part of the torso, which may cause disorders, such as pain, impaired judgment and, in serious cases, even unconsciousness. To counteract this effect, use is made of devices which prevent such body parts from swelling, such that they cannot receive additional blood. These devices originally consisted of laceable garments which surrounded the body parts and were so tightly strapped as to exert such a high external pressure on the body parts that these were unable to swell to any appreciable extent.

Since fighter aircraft have been developed to attain yet higher speeds and smaller turning radii, devices of this type have become out of date. The necessary pressures must then be so high that the devices cause considerable inconvenience if they are tight-fitting even when not required. Therefore, pilots have instead started using suits internally provided with double-walled casings, so-called bladders, which are filled with compressed gas so as to expand when pressure should be exerted on the body parts concerned.

In prior-art devices, the bladders are so designed as to cover the part of the body located below the waist and down to the ankles. To ensure proper function of the devices, one must have access to compressed air or any other gas in the aircraft, various valves and hoses for filling the bladders as well as a control system ensuring that the bladders produce an acceptable pressure on the body parts during flight.

One of the drawbacks inherent in the prior-art devices is that the flying suits become heavy and cumbersome. The use of bladders makes the suits very bulky. This depends, inter alia, on the fact that, in normal position, the bladders must often be maintained partly filled in order that the suit should react rapidly to changes of acceleration. They become rigid during flight, thus impeding the pilot's movement. Moreover, since the suits become very tight and warm, cooling is required.

These drawbacks will all be aggravated when aircraft development has come to the point that pilots should be able to withstand yet higher acceleration forces, which necessitates pressurizing additional parts of the body. The pressure-gas systems used and their mechanical components are already on the verge of reacting too slowly for the necessary rapid pressure increase to be achieved upon sudden changes of direction of the aircraft. In future aircraft generations, the drawbacks of these control systems will be increasingly pronounced.

To improve blood circulation, the known devices are of the same type as those used by pilots. Since the former also employ bladders, they too suffer from the same drawbacks, i.e. are complicated, heavy, rigid, and tight and react too slowly to be, for example, accurately controlled by the patient's cardiac rhythm.

SUMMARY OF THE INVENTION

The object of the present invention is to provide a device which is of the type stated above and which, in addition to solving the basic problems inherent in the prior art devices, has the following properties:

It should be easier to control the function of the device directly with the aid of electric control means, preferably without any pressure gas equipment, etc.

The device should have a total weight, including the control means, etc., which is less than that of prior art devices, be more flexible and less bulky than these.

The device should not suffer a complete loss of its function because of minor damage, which is the case in the prior known devices after a bladder puncture.

The device should allow air to pass through for removing moisture from the body.

The device should react more rapidly to acceleration changes than prior-art devices.

The foregoing objects are achieved in accordance with the present invention by the use of components of memory material in the device which may be an integrated part of a suit. The device may also be an individual piece of garment or several such pieces joined together, which enclose the body parts to be treated. The memory material may be included in the form of wires, thin strips or the like, for example, which by being heated to above a certain temperature return to a previously memorised shorter length or pass from one shape, e.g. the zigzag shape of a netting, into a memorised, different shape, for example a meander shape, whereby the pieces of garment shrink in the transverse direction and exert a pressure on the enclosed body parts. The heating of the memory-material components is preferably performed directly by conducting an electric current through the components, the resistance of which causes the heating, or indirectly by means of elements that may be located adjacent the components.

Memory materials, preferably metal alloys and polymers, have the specific capacity of enabling a deformation produced at a low temperature to recover by heating to a higher temperature. Thus, the material can "memorize" its initial shape.

In memory metals, the deformation is normally caused to occur at room temperature and the reverse deformation at a slightly higher temperature (generally <100° C.). In this manner, an apparently permanent deformation of up to about 8% elongation may recover. It may be noted that conventional metallic materials and alloys undergo permanent irreversible plastic deformation upon an elongation of even less than 0.1%. The deformation temperature and the possible size of the recovery of the shape depend on the composition of the alloy and how it has been produced. In a nickel-titanium alloy, this deformation temperature can be selected to be between 110° C. and 100° C. What is here described is "a one-way memory effect", which has been known for many years. This memory effect is caused by a phase transition in the alloy.

Less common is the "two-way memory effect", which appears in but a few alloys.

The type of alloy or the composition thereof then has two "memorized" configurations, one for a low and another for a high temperature range. Quite simply by raising and lowering the temperature, it is possible to repeatedly switch between one configuration and another. The two-way memory effect is best known for use with nickel-titanium alloys, which often also contain lesser amounts of other elements, in order that the correct properties, such as a certain deformation recovery temperature, should be obtained. The two-way memory effect is achieved by a special "training procedure", including a thermomechanical cycling process. The properties described make this type of memory metal especially suitable for use in a device according to the present invention.

There are polymers, such as mixed polymers of polybutadiene and polystyrene, which have similar memory properties as memory metals. Certain memory polymers can be made electrically conductive, having given electrical resistances. Thus, components of these materials may also be used with direct heating.

The components may themselves be parts of or make up the whole supporting structure of the device, for instance a coat-of-mail structure. However, use is preferably made of a base consisting of a flexible, layered material, such as textile, a tricot, a netting or a foil to support the components. These may be applied on the surface of the base or be integrated in the base, as woven-in threads or wires. If polymer components are used, these can be made to fit well together with a base of textile and also be integrated in the base. By using thin flexible wires of memory metal and a flexible base, it is possible to obtain a device which is readily adjustable to the pilot's body and which readily follows his movements. With direct heating, the wires are suitably electrically isolated from each other and provided with terminals to be connected to a power source and a control system. By means of such a device, the desired pressure can be exerted by the device "squeezing" the body part to be treated. The wires are electrically heated by a low voltage current to just above the deformation temperature, and then switch to a configuration, in this case a shorter length, that exerts the desired pressure. When the supply of electricity is interrupted, the wires are cooled and return to the relaxed configuration at the lower temperature.

To avoid discomfort by the heat from the wires, which will be heated to just above maximum cabin temperature, the wires are arranged so as not to be too close to the pilot's skin. The undergarments and insulating suits normally used by military pilots reduce the risk of such discomfort. This risk can be further reduced if, for example, the memory-material wires are combined with a system of electrically operated cooling elements which may act according to the Peltier principle for instance, or by using ventilating air in the suit. Cooling may also help reduce the time for return to the relaxed position of the wires.

A device according to the present invention may be designed as a garment. This garment may be composed of a base which at least partially is an approximately tubular casing adapted to enclose the body part to be pressurised, and may advantageously be openable and/or adjustable along a generatrix by means of, for example, one or more of the following means: zip fastener, lacing, or Velcro-strip fastener. The two parts of the adjusting or connecting means, such as the zip fastener halves, are attached to the base by means of reinforcements. If several such means are used, they may be located in different places on the garment.

Wires of memory material may be included in the base or may be applied to its exterior and fixed in the reinforcements where electric lines for feeding the wires may also be connected. The wires may extend substantially tangentially at right angles to the generatrices of the garment, such as from one reinforcement to another. Since the wires, upon activation, shrink the textile between the reinforcements, the garment will exert a pressure on the body part. If an adjusted pressure is desired, the above-mentioned single wire, for example, which extends around the device or the garment, may be divided into a number of wires which in insulated, direct or indirect fashion, grasp each other. Since current is supplied individually to each wire or group of wires, the desired shrinkage can be controlled and obtained. Instead of individual wires, it is possible to use wires having an extent also along the garment, such as by being wound as in a second preferred embodiment of the present invention.

As previously mentioned, a transformation to another "remembered" shape of the component may also be used. The components can then be represented by wires with a zig-zag form which together constitute a net of the type which is, for example, used in wire fencing. By heating the wires, these can be made to reshape into, for example, a meander curve, which is common in slowly flowing rivers. By causing the straight parts of the zig-zag curves to take up an "S" form, a shrinkage of the garment surface may be obtained. With a correctly remembered meander curve the net can cause the garment to contract in the transverse direction even if the major direction of the wires is not parallel to the longitudinal axis of the garment as in the article described below.

A further method to use the transformation to another "remembered" shape is exemplified by the use of a screw- or spiral-formed spring. This can, when activated normally by heating, be required to take a greater length in the unrestricted condition. If the spring is however hindered or prevented from freely expanding, it acts as a pressure spring with an axially directed force. The spring can, in this way, act against the surface of a part of the body and thereby exert a pressure. A garment containing such a type of spring can have an outer and an inner flexible layer between which the spring is placed at right angles to the layers and fixed at its ends. The outer layer, which is to restrict expansion of the spring is of a stiff material. The inner layer, which is to distribute the pressure over the surface of the part of the body may preferably be made of an elastic material. The number of such springs is determined by the size of the body part on which the pressure is to be exerted.

The action of the components is not necessarily direct, as in the examples described above. The component can alternatively create a pressure indirectly, for example by acting on a mechanism which in turn applies a pressure via the garment. The mechanism may contain a mechanical element such as an angled lever or a wedge which pulls together the substantially cylindrical formed garment round the part of the body to be treated. This can be constructed in a way such that the above described reinforcement at the openings of the approximately tube-formed shell are pulled towards each other with the aid of the mechanism. The advantage of this alternative is that the pressure generated and the degree of shrinkage of the garment in the transverse direction can be adjusted by means of the mechanism.

The present invention offers many advantages over the prior art devices. Since the function of the device according to the invention is preferably controlled directly by electricity through electric heating, the device can easily be integrated in the other control system of an aircraft. Since air gas devices are avoided, a lighter and considerably less complex control system is obtained for the pressure exertion. The memory-material wires included in the device and the pertaining auxiliary means weigh much less and are less space-consuming in a suit than with the bladders, with auxiliary means, of the prior-art devices. Moreover, the suits do not become as stiff as with the known devices. If the device is damaged by splinters and the like, it will still be functioning properly as opposed to a suit with bladders, since all the memory-material wires are scarcely likely to be destroyed at the same time.

Modem military aircraft can be subjected to an acceleration increase of 6 g/s. The time for attaining the maximum acceleration of 12 g may therefore be only 2 s. The known systems with mechanical compressed-air means involve such a high inertia that their reaction time is much longer than this time as opposed to the device of the invention which, with its small thermal mass and direct control, has a very short reaction time. The reaction time of memory-material wires depends on the time required for attaining the deformation temperature. Using memory metal and direct electric heating, this time becomes very short, less than 1 s. Tests have shown that times down to 0.2 s are possible. For recovery, it is merely required that cooling occurs to a temperature just below the deformation temperature, and so this time too may be made very short, only a few seconds or less, without the use of cooling.

As a result of the device of the present invention, it is possible, in a simple and efficient manner, to control the pressures to be exerted on the pilot. By individual activation of the different wires in the device, different portions of the same body part can be affected differently, as opposed to the case of prior-art devices. For example, it may be advantageous to increase the pressure in a pilot's leg stepwise from below as the acceleration forces increase. The pressures exerted on the body parts can be measured with sensors. On the basis of information derived therefrom, a control system included in the steering system of the aircraft can adjust the pressures to be as optimal as possible.

The control system can be programmed differently for different pilots. By data processing of control values, the device can, because of its rapid reaction ability, even anticipate acceleration forces so that the pressure exertion can be increased slowly even before the need arises with a view to minimizing the pilot's discomfort by the pressure increase. By the flexible control function, it is easy to have the device cooperate with bladders of known type for instance, which are preferably used on the upper part of the pilot's body when pressure assisted breathing is employed. A further advantage of the device is that the pilot, thanks to the short reaction time, will have good support for the spinal column in the case of catapult ejection, despite the fact that the time between release and ejection is extremely short.

Similar advantages are gained when using the device for improving blood circulation. Since the device according to the invention has such a short reaction time, it can readily be controlled so as to "squeeze" at a rate determined by such things as the cardiac rhythm of the patient. By means of the above-mentioned feedback function with the aid of sensors and computer processing of control signals, a medically optimal pressure exertion can be obtained.

BRIEF DESCRIPTION OF THE DRAWINGS

Preferred embodiments will be described in more detail hereinafter with reference to the accompanying drawings, in which like reference numerals designate like parts in the different figures.

DESCRIPTION OF THE PREFERRED EMBODIMENTS

Figure 1:
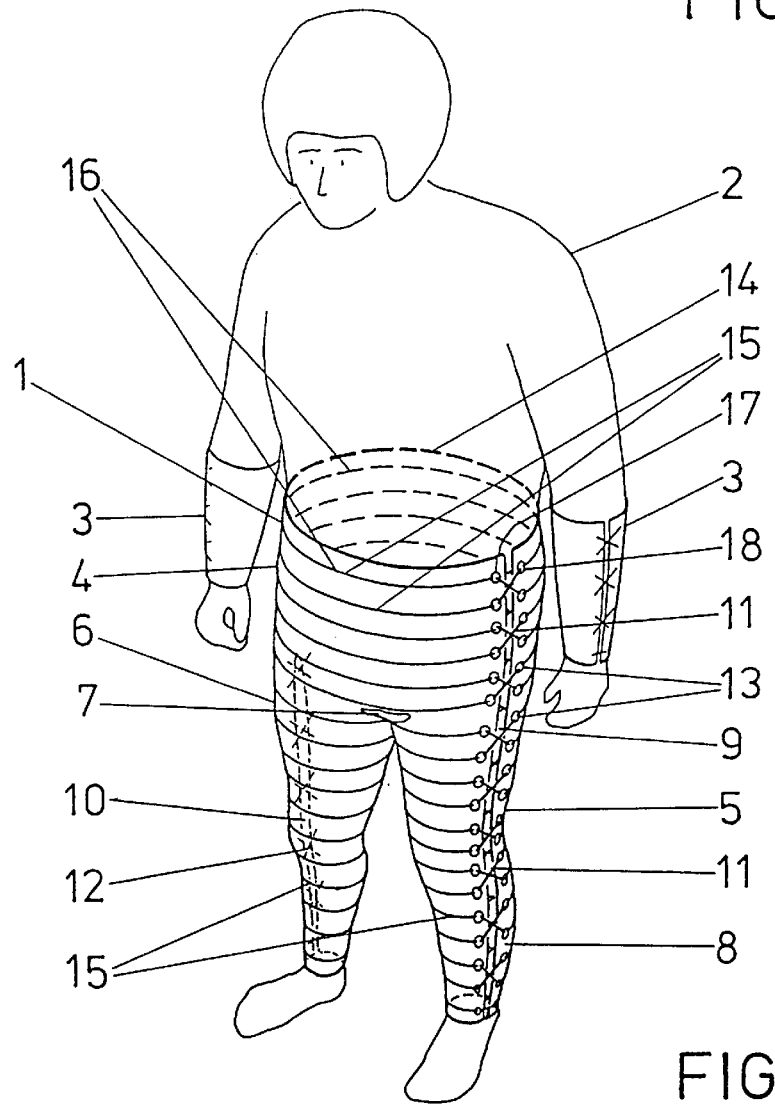
FIG. 1 is a perspective view of a trouser garment having memory-metal wires according to the device of the present invention to prevent blood pooling in the lower part of a pilot.

In FIG. 1, the device of the present invention is shown in the form of a pilot's trouser garment 1. The device is of the "overall" type which according to future requirements must be able to exert a pressure on the whole of the lower part of the pilot's body from the waist down to the ankles, with the exception of the buttocks region which is pressurised when the pilot is sitting. The trouser garment is included in the pilot's combat suit, which also includes an insulating suit 2, protective means 3 against painful swelling of the forearms as well as a garment for the upper part of the body for balanced overpressure breathing, and a special foot wear. The garment for the upper part of the body and the foot wear are of known designs and are not shown in the Figure. The protective means 3 for the forearms may also be designed in accordance with the invention. Moreover, the pilot wears a protective overall (not shown) covering all the above-mentioned garments except the foot wear.

In terms of construction, the trouser garment 1 may be divided into three main parts which are joined together: an abdominal belt 4 intended to surround the torso from the waist down to the crotch, as well as a left trouser leg 5 and a right trouser leg 6 intended to surround the pilot's legs. In the crotch, the abdominal belt and the legs are separated by a space 7 in said buttocks region. Each main part is tubular and basically built up in the same way. They have a supporting base 8 conformed to the shape of the pilot's body and preferably consisting of woven textile or a tricot which should preferably be readily permeable to air. To enable the pilot to put on the garment and to have it conformed to the shape of his body, the parts have openable joints consisting of gaps 9 and 10 as well as lacings 11 and 12 on the abdominal belt 4 and left trouser leg 5 and the right trouser leg 6, respectively. The lacings are attached in any known manner in pairwise opposite eyelets 13 at the edges of the base adjacent the gaps.

The gap 9 of the belt 4 is designed as a small opening which extends along the left-hand side of the garment down from the waistband 14 and continues as the gap of the left-hand trouser leg down to its termination near the ankle. The gap 10 of the right-hand trouser leg is designed as a gap which extends from the termination near the ankle up to the transition between the abdominal belt and the trouser leg.

At even intervals, parallel to each other, memory-metal wires 15 with the two-way memory effect are arranged on the outer surface of the base 8. The wires are attached to this surface such as by being sewn to it throughout the entire length thereof. At its ends, each wire is fixed in each of the pairwise opposite eyelets. The uppermost wire 16 in the abdominal belt 4 is thus fixed in the uppermost front eyelet 17, extends around substantially the entire abdominal belt parallel to its waistband 14 and is fixed in its other end in the uppermost rear eyelet 18. When the wires are subjected to shrinkage, the base will also shrink in the tangential direction, thus pressurising the body part. By placing the wires on the abdominal belt base, one gains the advantages that heat can easily be dissipated by natural or forced convection, such as by supplying ventilation air between the trouser garment and the protective overall, and also that the abdominal belt base serves to distribute the pressure from the wires more evenly over the body.

Figure 2:
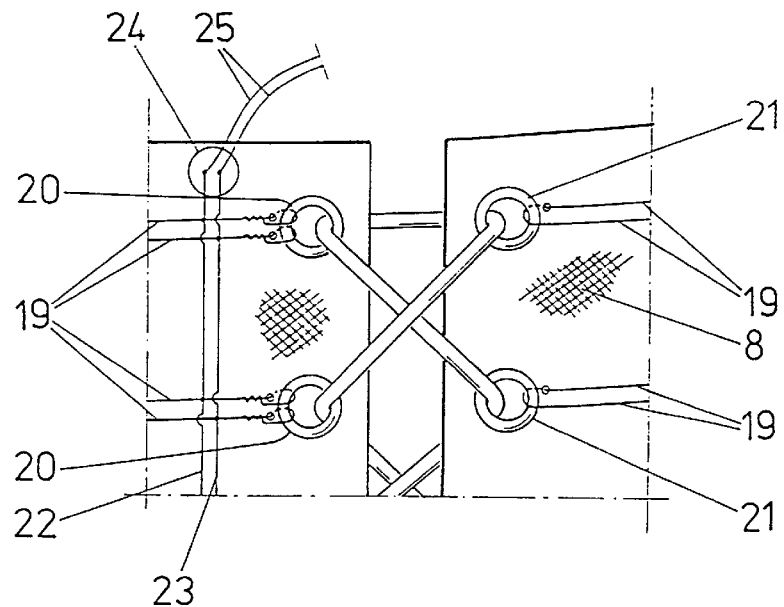
FIG. 2 shows in more detail the upper part of the left side of the trouser garment.

FIG. 2 shows in more detail the use of doubled wires 19 of memory metal and their supply with electricity. The ends of the wires are fixed in the front eyelet 20. When doubling the wires, these are passed through the rear eyelets 21. The Figure schematically shows how, at the front eyelets, a line 22 for supplying electricity is connected to the upper one of the doubled wires and a discharge line 23 is connected to the lower one of the same wires 19. The supply and discharge lines extend from a connecting means 24, to which a control line 25 from a control unit in the aircraft is connected. As earlier mentioned, all the wires of the garment are suitably distributed for different areas, each of which is supplied by different pairs of supply and discharge lines, which are all connected to a connecting means. The pressure exertion can then be controlled individually for the different regions of the body parts.

Figure 3:
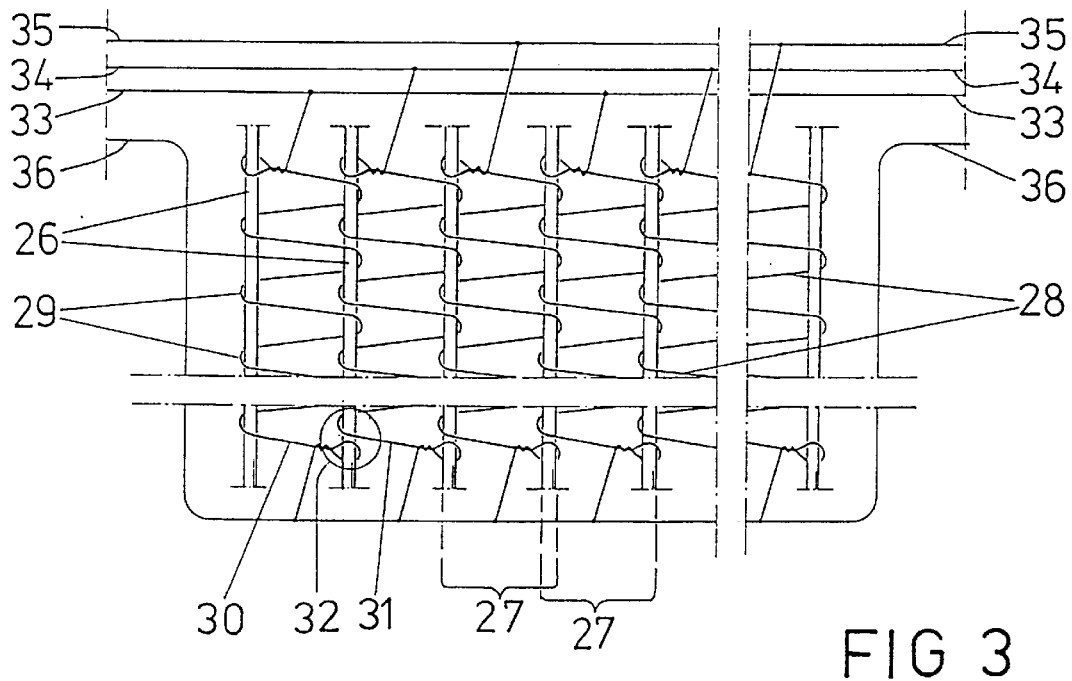
FIG. 3 shows an alternative arrangement of the memory-metal wires.

FIG. 3 shows an alternative arrangement of the memory-metal wires in the garment. The advantage of this design is that the size of the pressure exertion can be varied, in that the wires of one area have been distributed in the transverse direction of the garment, and in that the different parts can be supplied with current individually. In the textile base, strong delimiting supporting yarns 26 have been woven in parallel with each other in the longitudinal direction of the garment. Around parts 27 of the textile base, delimited by two suitably separated supporting yarns, memory-metal wires 28 are wound along the surface so as to be bent around the delimiting supporting yarns 26. By arranging the wire loops 29 formed at the bends relatively close to each other, these wires will have a direction extending substantially transversely to the longitudinal direction of the garment. In the Figure, the distance between the loops has been exaggerated for greater clarity. If the wires 30, 31 of juxtaposed parts comprise the same supporting yarn, the wires and the yarns will grasp each other in connections 32 so as to form a coherent netting integrated in the supporting base. When the wires are activated, the textile base will shrink uniformly in the transverse direction of the garment. This design can be varied, such as by winding the wires around supporting yarns that are not located adjacent each other, such that the bends of the wires pass inwardly of each other, or by completely dispensing with the supporting yarns and having the loops of adjacent wires engage in each other as in the wire netting of a fence. In the latter case, the zigzag-shaped wire may extend diagonally over the diagonal direction of the garment.

The memory-metal wires shown in FIG. 3 are attached at both ends to supporting yarns for taking up tractive forces. For the supply of electricity for direct heating, the wires are divided into a number of separate groups, each of which is separately supplied from the control unit. In the design shown, they are divided into three groups, each comprising, taken in order, every third wire and separately supplied by a respective one of three supply lines 33, 34 and 35. The wires of each group are connected at one end to the supply line of the group and at the other end to a common discharge line 36. By supplying current to one, two or all three groups, the shrinkage can be varied. If materials having different shrinkage properties are used in the wires of the three groups, it is possible by different combinations to control the shrinkage within wide limits. If the supply and discharge lines are connected to the control unit at both ends, the device is highly insensitive to damage, such as rupture of any of the above-mentioned lines.

Figure 4:
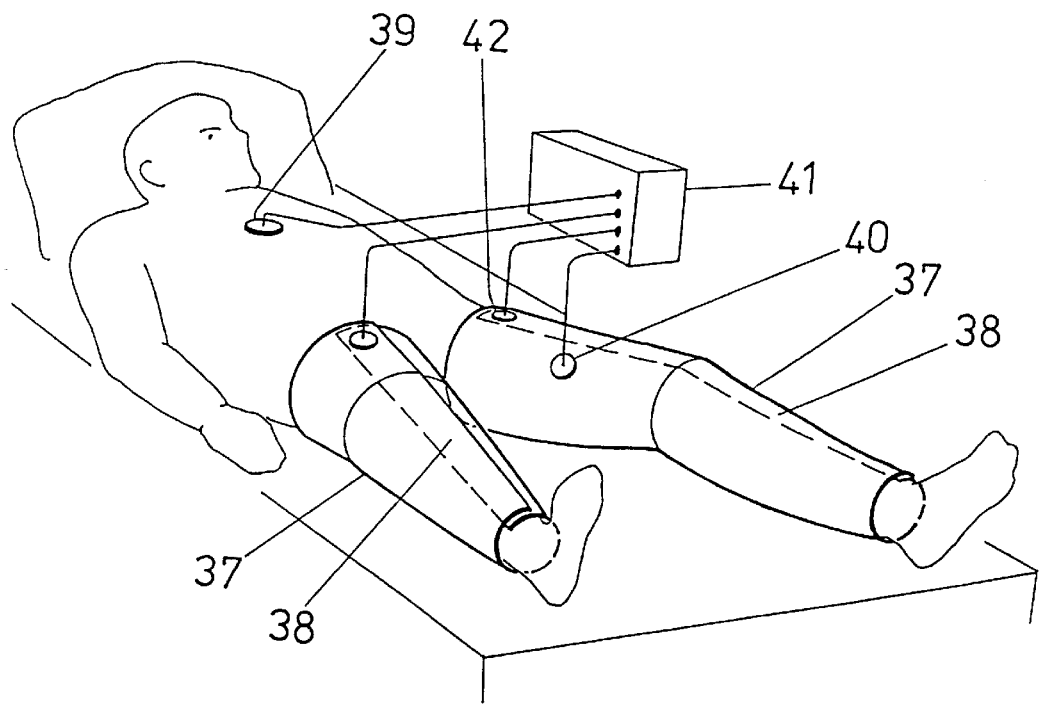
FIG. 4 is a perspective view of a device for improving the blood circulation of a patient.

FIG. 4 shows devices for improving blood circulation, which consist of leg sleeves 37. These are tightened with good fit on the patient's legs by means of such as Velcro-type strip fasteners at overlaps 38 throughout the entire length of the sleeves. The sleeves are designed in the same way as the pilot's garment described above. By means of signals from a transducer 39 recording the cardiac rhythm of the patient, and from at least one feedback sensor 40 of the pressure exerted by the device, a computer in a control unit 41 determines the control currents which via lines and connecting means 42 are led to the assemblies of memory-metal wires existing in each leg sleeve. Since these wires are distributed in different areas and react rapidly to control currents, the leg sleeves can, on different parts of the legs, exert pressures which are individually determined as to size and time for optimal treatment.

Figure 5A:
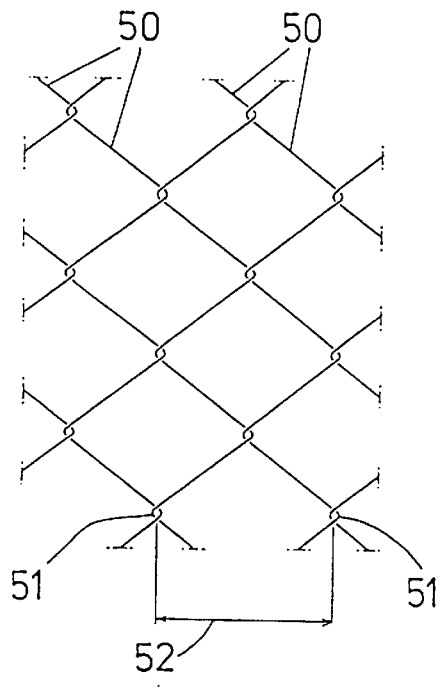
FIG. 5a and FIG. 5b illustrate one alternative with which the shape memory metal wires act by a change in shape or geometry. The wires are in FIG. 5a in the relaxed condition and in FIG. 5b in the activated condition.
Figure 5B:
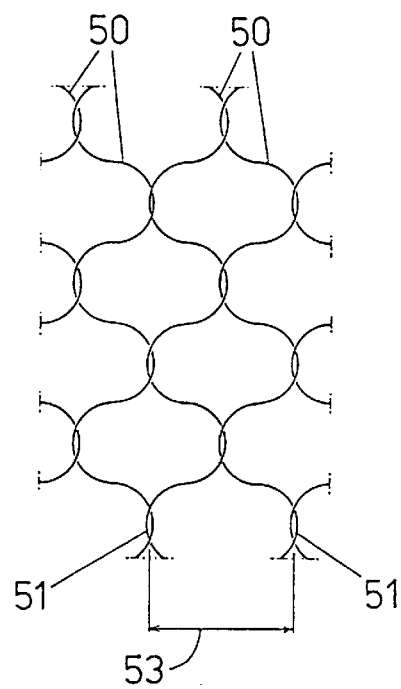

In FIG. 5a and FIG. 5b are illustrated one form of the invention in the shape of a wire net. The net itself may constitute a load carrying structure as in the form of links which comprise the garment, or may be fixed to a base as in the above example. The components consist of shape memory alloy wires 50 with their major direction in the length of the garment. In FIG. 5a the wires 50 are illustrated in the relaxed condition. The zig-zag or saw-tooth shape wires are laid parallel with each other and thus form a net since the corners in one wire are fixed at the intersection 51 with the corresponding corners in a neighboring wire. FIG. 5b shows the wires in the taut and pressure generating condition. The wires have taken-up a remembered meander curve form in which the straight sections between the bends have transformed to an "S" shape. The distance between the connections 51 has in this way decreased from a distance denoted 52 in the relaxed condition to a distance 53 in the pressure generating condition. The garment therefore shrinks in the transverse direction. With the correct meander curve form, no shrinkage occurs in the longitudinal direction. The wires do not necessarily have their major dimension or length in the longitudinal direction of the garment. For example, if the net is rotated about 45° from this direction, only the zig-zag shape wires which lie transverse to the longitudinal direction of the garment are required to "remember" how to transform to the "S" shape. The other parts of the zig-zag wires may remain straight.

Figure 6:
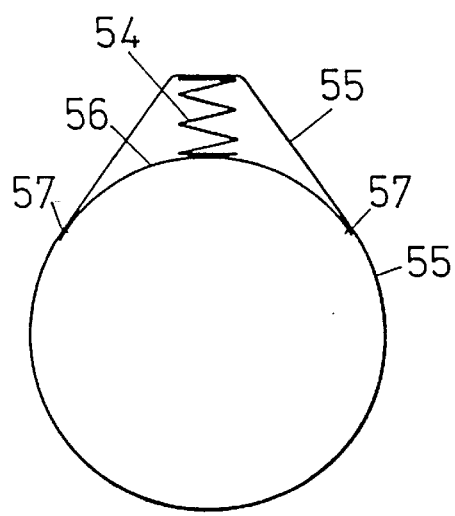
FIG. 6 shows in cross-section an example of a garment containing the present invention in the form of a sprial-formed component.
Figure 7:
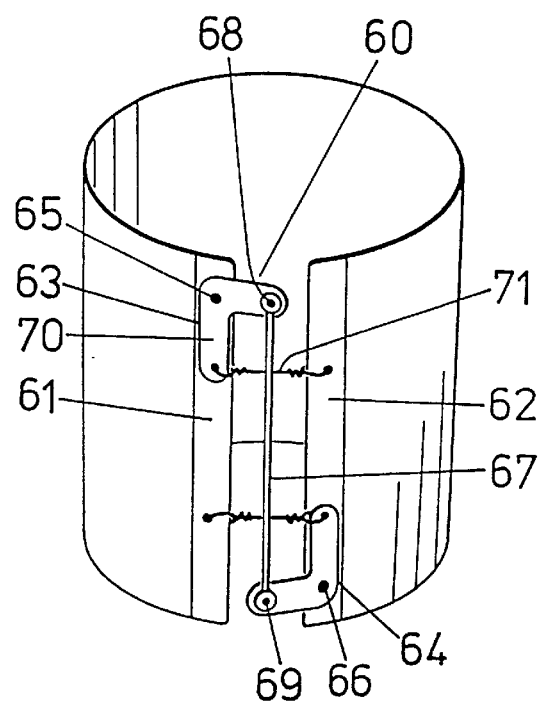
FIG. 7 shows in perspective an alternative form of the invention in a tube-shaped part of a garment which applies pressure by means of a 90° lever.

FIG. 6 illustrates an application of the present invention in the form of a component which is trained to expand to create a pressure, as described above. The garment, which contains a screw or spiral formed spring 54 of shape memory metal has an outer layer 55 with low elasticity covering the spring, and between the spring and the part of the body to be treated an inner layer 56 of preferably a more elastic material. The outer layer is arranged so as to restrict the expansion of the spring and in this way create the required pressure. The inner layer may be fastened to the outer layer with for examples seams 57. In the example illustrated, the outer layer may completely surround the part of the body. If pressure is required to be applied to the entire body part, an arrangement may be used which resembles a spring mattress which is wound around the body part with spiral springs as components. When these are heated their expansion is restricted by the stiff outer layer, which serves to restrain the springs, which press against the inner layer and thereby apply pressure on the body part.

In yet another method, the components are allowed to work a mechanism which in its turn creates the outer pressure on the body part. This may be achieved from the substantially cylindrical formed part of the garment of a reasonably stiff material which has an opening 60. The garment edges at this opening are equipped with two elongated reinforcements, 61, 62. Pressure application is obtained when the mechanism forces these reinforcements towards each other. The mechanism contains two similar 90° levers, 63, 64 which at the corners are equipped with bearings in each respective reinforcement in the form of rivets, 65, 66. The lever arms have in each case their first arm directed in towards the opening 60. In these arms a shape memory metal component 67 shaped as a piston rod is equipped with bearings in the form of rivets 68, 69. The other end of each lever arm 70 is directed parallel with, and towards the central part of the reinforcement 61 in which the lever arm 63 is allowed to rotate. This second arm 70 is attached to the opposite reinforcement 62 with a link 71. By requiring the component to contract on activation a pressure may be created. If on the other hand the other arm is turned in the opposite direction, that is to say away from the reinforcements central part, the shape memory metal component must be required to remember to expand in order that a pressure be generated. Both lever arms may also be equipped with bearings in the same reinforcement, and in this case both links are fixed in the same, opposite reinforcement.

We claim:

1. A device for exerting an external pressure on a part of a human body comprising a garment being adapted to surround the body part in a form-fitting manner and including at least one component of memory material which, by heating, changes its shape so as to bring about a contraction of said garment and, by cooling, returns to a previous shape so as to interrupt said contraction.

2. A device as claimed in claim 1, wherein said component is adapted to be heated by conducting electric current therethrough.

3. A device as described in claim 1, wherein said component is memorized to shorten to change its shape by heating.

4. A device as claimed in claim 1, wherein said component includes at least one wire which is memorized to shorten in length by heating.

5. A device as described in claim 1, wherein said component includes at least one thin strip memorized to shorten in length by heating.

6. A device as described in claim 1, wherein said component of memory material is made of a metal and said device further comprises a mechanical element influenced by said component to pull together said garment to exert the pressure upon heating of said component.

7. A device as described in claim 1, wherein said component is adapted to bend to change its shape.

8. A device as claimed in claim 1, wherein said component is initially formed in zig-zag shape and is memorized to form a meander shape by heating.

9. A device as claimed in claim 1, wherein said component includes at least one screw (spiral) formed spring which is memorized to expand by heating when in an unrestricted condition.

10. A device as claimed in claim 1, wherein said garment is substantially tubular when in use.

11. A device as claimed in claim 1, wherein said garment includes a flexible base and said component is disposed about said base.

12. A device as described in claim 1, wherein said component is at least part of a support structure for said garment.

13. A device as claimed in claim 4, wherein said base is made of a generally fiber material and that the memory material is a metal material.

14. A device as described in claim 12, wherein said component of memory material is made of a polymer.

15. A device as claimed in claim 1, wherein said garment includes a number of said components, each of said components forming a part of the garment, said parts arranged substantially in a row aligning said parts adjacently in a direction of the contraction, each adjacent part electrically insulated in connection with a next adjacent part, and each of said number of components selectively connected to individual electric current lines for selectively supplying current to said components to heat said components.

16. A device as claimed claim 1, further comprising a sensor for measuring the exerted pressure.

17. A device as claimed in claim 1, wherein said device is adapted to be connected to a control unit in an aircraft and adapted to exert the pressure on the body part, and the pressure is determined by the control unit arranged to sense G-forces.

18. A device as claimed in claim 1, wherein said device is adapted to be connected to a control unit and adapted to exert the pressure by recurring contraction on a basis of signals received from the control unit, said device further including a transducer adapted to sense the cardiac activity of the human body and communicate with the control unit.

19. A device for exerting an external pressure on a part of a human body comprising a supporting base being adapted to surround the body part in a form-fitting manner, a component of memory metal, and a mechanical element influenced by said component to pull together said base to exert the pressure upon heating of said component.

20. A device for exerting external pressure to a human body part, comprising at least one component of memory material which changes its shape upon activating to cause the device to exert said pressure on the body part and upon deactivating to discontinue said pressure.

21. A device as described in claim 20, wherein said component is associated with a base adapted to conform to a shape of the body part.

22. A device as described in claim 20, wherein said component is connected to a control unit for controlling the pressure exerted.

23. A device as described in claim 21, wherein said base is substantially tubular in shape.

24. A device as described in claim 20, wherein said component of memory material is adapted to be activated by conducting electricity therethrough.

25. A device as described in claim 20, wherein said device includes more than one said component, each of said components forms a part of the device, said parts aligned adjacently in a row in a direction of contraction of the device while exerting said pressure on the body part, and each of said components are electrically insulated from the others and are adapted to be selectively connected to electrical current supply lines for heating said components.

26. A device as described in claim 20, wherein said device includes two or more components that are connected to a control unit and further includes a pressure sensor for measuring the pressure exerted on the body part, and said control unit is used to select an amount of current supplied to each of said components.

27. A device as described in claim 20, wherein said device includes a transducer adapted to measure cardiac activity of an animate body of the body part, said device connected to a control unit to exert pressure in recurring contractions based upon evaluation of information by the control unit.

28. A device as described in claim 20, wherein said component of memory material is a metal alloy.

29. A device as described in claim 20, wherein said component of memory material is a polymer.

30. A device as described in claim 20, wherein said component includes at least one wire which is memorized to shorten in length by activating and exert the pressure to the body part.

31. A device as described in claim 20, wherein said component includes at least one strip which is memorized to shorten in length by activating and exert the pressure to the body part.

* * * * *